(12) United States Patent
Smith

(10) Patent No.: US 11,324,524 B2
(45) Date of Patent: May 10, 2022

(54) FOOT AND ANKLE SURGICAL METHOD AND APPARATUS THEREFOR

(71) Applicant: VFAS International Holdings Pty Ltd, Marrackville (AU)

(72) Inventor: Neil Robert Smith, Marrackville (AU)

(73) Assignee: VFAS International Holding Pty Ltd, Marrackville (AU)

( * ) Notice: Subject to any disclaimer, the term of this patent is extended or adjusted under 35 U.S.C. 154(b) by 0 days.

(21) Appl. No.: 16/290,688

(22) Filed: Mar. 1, 2019

(65) Prior Publication Data

US 2020/0187964 A1 Jun. 18, 2020

(30) Foreign Application Priority Data

Dec. 12, 2018 (AU) .................................. 2018904720

(51) Int. Cl.
*A61F 5/01* (2006.01)
*A61B 17/17* (2006.01)
(Continued)

(52) U.S. Cl.
CPC .......... *A61B 17/1775* (2016.11); *A61B 34/10* (2016.02); *A61F 5/0111* (2013.01);
(Continued)

(58) Field of Classification Search
CPC ....... A43B 7/141; A43B 7/142; A43B 17/006; A43B 7/144; A43B 7/1445; A43B 7/14;
(Continued)

(56) References Cited

U.S. PATENT DOCUMENTS 4,886,258 A * 12/1989 Scott ...................... A61G 13/12
5/624
7,367,074 B1 * 5/2008 Bergquist ................. A43B 7/28
12/142 N
(Continued)

FOREIGN PATENT DOCUMENTS

CN 203425024 U * 2/2014

OTHER PUBLICATIONS

Cheng et al., Nonlinear Finite Element Analysis of the Plantar Fascia due to the Windlass Mechanism, Aug. 1, 2008 [retrieved Jun. 22, 2020], Foot & Ankle International, vol. 29, No. 8, pp. 845-851. Retrieved: https://journals.sagepub.com/doi/full/10.3113/FAI.2008. 0845 (Year: 2008).*

(Continued)

*Primary Examiner* — Matthew C Bella
*Assistant Examiner* — Dennis Rosario
(74) *Attorney, Agent, or Firm* — Baker Botts L.L.P.; Michael A. Sartori

(57) ABSTRACT

A weight-bearing stance corrected foot orthotic (12) is adapted to be used on the foot (2) of a anaesthetised patient in the supine or prone position, the weight bearing stance corrected foot orthotic (12) adapted to dorsiflex the toes of the forefoot of the patient an angle of between 30° to 50° to the plane of the foot (2). A surgical foot orthotic (12) is formed by the steps of disposing a patient's foot (2) or both feet in a weight bearing neutral position and dorsiflexing the forefoot or forefeet of the patient such that patient's foot (2) or feet are in or towards the Windlass configuration. A first orthotic (5) correcting the stance of the patient in the weight bearing position with dorsiflexed forefoot is formed and this is scanned to form an electronic image of the corrective load bearing surface. The electronic image is modified to include one or more guide apertures or cut-outs (9) and a surgical (Continued)

corrected weight-bearing orthotic from the modified electronic image is 3-D printed with the one or more guide apertures or cut-outs.

8 Claims, 14 Drawing Sheets

(51) Int. Cl.
| | |
|---|---|
| *A61F 5/37* | (2006.01) |
| *A61B 34/10* | (2016.01) |
| *B33Y 10/00* | (2015.01) |
| *B33Y 80/00* | (2015.01) |
| *B29C 64/386* | (2017.01) |
| *B29L 31/00* | (2006.01) |
| *A61B 17/56* | (2006.01) |
| *A61B 17/00* | (2006.01) |
| *B29K 77/00* | (2006.01) |

(52) U.S. Cl.
CPC .............. *A61F 5/37* (2013.01); *B29C 64/386* (2017.08); *B33Y 10/00* (2014.12); *B33Y 80/00* (2014.12); *A61B 2017/00526* (2013.01); *A61B 2017/564* (2013.01); *A61B 2017/567* (2013.01); *A61B 2017/568* (2013.01); *A61B 2034/102* (2016.02); *A61B 2034/108* (2016.02); *B29K 2077/00* (2013.01); *B29L 2031/753* (2013.01)

(58) Field of Classification Search
CPC .... A43B 7/20; A43B 7/22; A43D 1/02; A43D 1/022; A43D 2200/60; A61B 5/1036; A61B 5/1074; A61B 5/1077; A61B 5/1038; A61B 5/1079; A61B 5/0077; A61B 5/1078; A61B 34/10; A61B 2034/102; A61B 17/1775; A61B 17/151; A61B 5/6807; G06F 30/00; A61F 2/6607; A61F 2/66; A61F 5/0127; A61F 5/0111; A61F 5/01; A61F 5/0102; A61F 5/0195; A61F 2/76; A61F 13/045; A61H 3/00; A61H 2003/007; A61H 1/0262; A61H 1/0266; A61H 2201/164; A61H 2205/12; G06T 2210/41

See application file for complete search history.

(56) References Cited

U.S. PATENT DOCUMENTS

| | | | | |
|---|---|---|---|---|
| 8,066,656 | B2* | 11/2011 | Bonutti | A61H 1/02 |
| | | | | 602/23 |
| 8,366,789 | B2* | 2/2013 | Summit | A61F 2/66 |
| | | | | 623/27 |
| 8,480,760 | B2* | 7/2013 | Hansen | A61F 2/6607 |
| | | | | 623/47 |
| 9,817,439 | B2* | 11/2017 | Gosieski, Jr. | G06F 1/163 |
| 10,231,862 | B2* | 3/2019 | Summit | A61F 5/013 |
| 10,357,416 | B2* | 7/2019 | Cole | A61G 13/1255 |
| 2016/0331071 | A1* | 11/2016 | Kane | A43D 1/02 |
| 2017/0246338 | A1* | 8/2017 | Taylor | A61F 2/7812 |
| 2017/0273397 | A1* | 9/2017 | Smith | A43D 1/022 |

OTHER PUBLICATIONS

Handelsman et al., Supramalleolar wedge osteotomy: a method of correcting fixed equinus and associated deformities in children, Mar. 2005 [retrieved Jun. 22, 2020], The Foot, vol. 15, Issue 1,pp. 33-39. Retrieved: https://www.sciencedirect.com/science/article/pii/S0958259204000975 (Year: 2005).*

Korda et al., When to consult the podiatrist, Aug. 2004 [retrieved Jun. 22, 2020], Best Practice & Research Rheumatology, vol. 18, No. 4,pp. 587-611. Retrieved: https://www.sciencedirect.com/science/article/pii/S1521694204000531 (Year: 2004).*

Webpage entitled: Ankle, Foot & Orthotic Centre: Subtalar Arthritis, 5 pages, copyright 2021 [retrieved Feb. 13, 2021], Retrieved: https://ankleandfootcentre.com.au/subtalar-arthritis/ (Year: 2021).*

Webpage entitled: Transverse tarsal joint, 3 pages, edited Nov. 27, 2018 [retrieved Feb. 13, 2021], Retrieved: https://en.wikipedia.org/wiki/Transverse_tarsal_joint (Year: 2018).*

Webpage entitled: Foot Education: Bones and Joints of the Foot and Ankle Overview, edited Oct. 17, 2015 [retrieved Feb. 13, 2021], 12 pages. Retrieved: https://footeducation.com/bones-and-joints-of-the-foot-and-ankle-overview/#calcaneus (Year: 2015).*

Machine translation of CN-203425024-U, retrieved Jul. 29, 2021, 10 pages. Retrieved: https://patents.google.com/patent/CN203425024U/en?oq=cn203425024 (Year: 2021).*

Johnson et al., Plantar Fasciitis What Is the Diagnosis and Treatment?, Jul./Aug. 2014 [retrieved Jul. 30, 2021], Orthopaedic Nursing, vol. 33, No. 4, pp. 198-204. Retrieved: https://nursing.ceconnection.com/ovidfiles/00006416-201407000-00007.pdf (Year: 2014).*

* cited by examiner

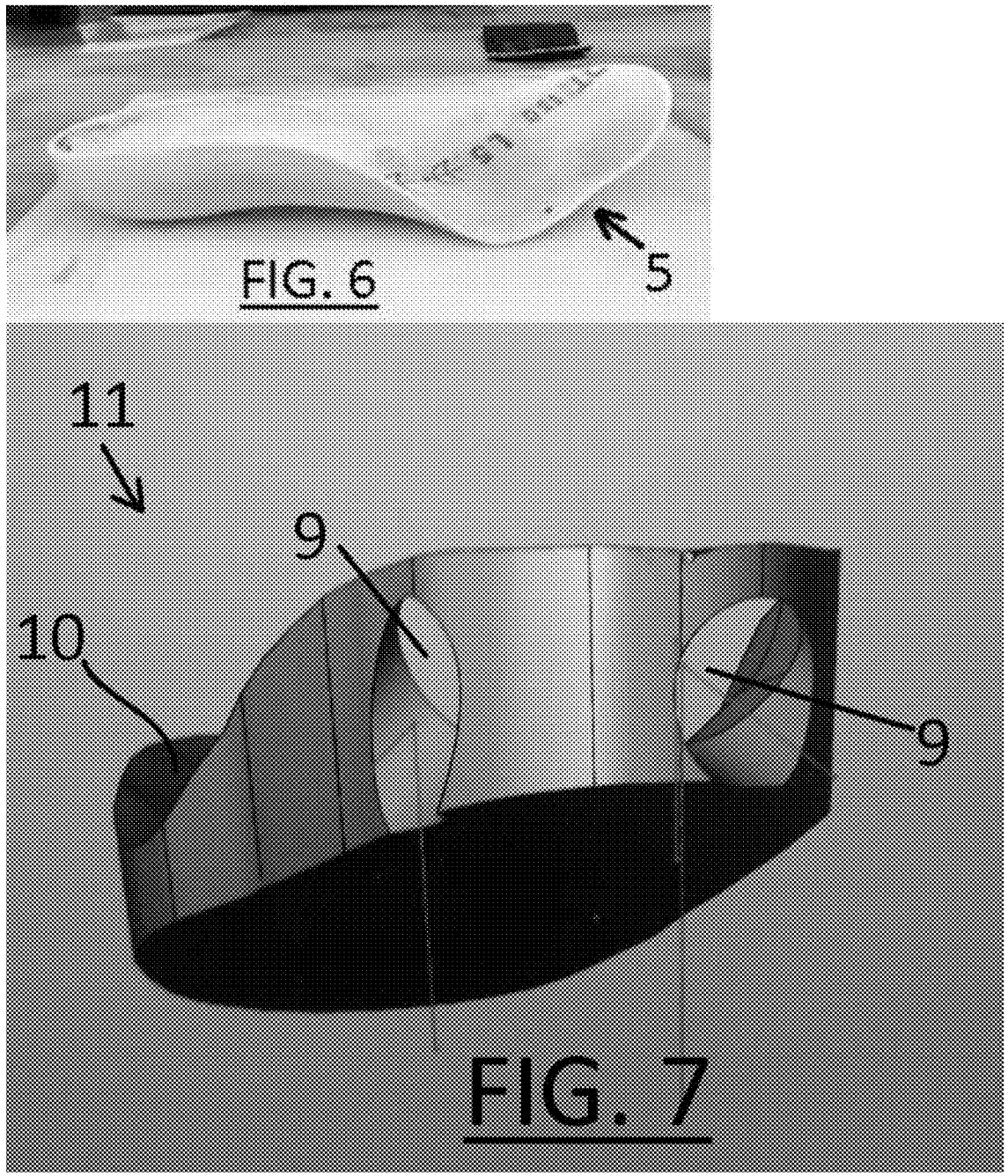

FOOT AND ANKLE SURGICAL METHOD AND APPARATUS THEREFOR

FIELD OF THE INVENTION

The invention relates to correction of foot or ankle conditions and, in particular, to a method of performing corrective foot or ankle surgery and an apparatus for use with the surgery.

The invention has been described with reference to corrective ankle surgery and will be described hereinafter with reference to this application. However, it will be appreciated that the invention is not limited to this application and is applicable to foot and lower leg surgeries.

BACKGROUND OF THE INVENTION

The foot and ankle of the body of a person is a precise and complex structure. There are, in each foot, 26 bones, 33 joints of articulation and over a 100 tendons, muscles and ligaments. Serious feet and ankle injuries requiring surgical repair are all too common. These can be caused by a host of factors such as trauma or excessive loading, foot deformities, arthritis, and poor movement patterns when conducting everyday activities.

In view of the complexities of foot anatomy and precise loading requirements for proper use, it will be appreciated surgical repair can be anything but straightforward. For example, when a foot or ankle includes multiple fractures such as in the foot arch or the calcaneus to which the plantar facia anchors. In such cases, the foot or ankle by virtue of the fractures (or any other problem providing similar symptoms) is moved or deformed into an undesirable state whether at rest or under some load.

When foot surgery is performed it occurs in a sterile operating room theatre on an operating table. The patient can be laying either prone (facing down) or supine (facing up) on the operating room table. So far as surgeries are conducted with the patient under anaesthetic (most often a general) the bones of their foot are at rest where the structures within the foot are relaxed. This is known to be problematic for foot and ankle surgeons because the foot is not in natural alignment during surgery.

Often the surgeon is reliant upon their experience to simulate foot alignment intra-operatively to position the foot. That is, based on significant training and practical experience, surgeons essentially improvise and align the foot as they expect it to be arranged when bearing weight. This may lead to malposition which can impact the fusion rate of bone fractures being repaired and affect the final outcome of the surgery for the patient. When fusions are performed, the articulation of the joints is extremely important for, not only walking and other everyday activities, but also the effect this has on the structures above the foot that are affected by the foot's position and alignment. It is well known that if one or both feet are in poor alignment, it can cause excessive, internal or external rotation which puts increased loading on the ankles, knees, hips and back.

GENESIS OF THE INVENTION

The genesis of the invention is a desire to provide a foot &/or ankle surgical method and apparatus therefor that will overcome one or more of the disadvantages of the prior art, or to provide a useful alternative.

SUMMARY OF THE INVENTION

According to a first aspect of the invention there is provided a method of forming a surgical foot orthotic, the steps including:
disposing a patient's foot or both feet in a weight bearing neutral position;
dorsiflexing the forefoot or forefeet of the patient such that patient's foot or feet are in or towards the Windlass configuration thereof;
forming a first orthotic correcting the stance of the patient in the weight bearing position with dorsiflexed forefoot;
scanning the first orthotic and forming an electronic image of the corrective load bearing surface thereof;
modifying the electronic image to include one or more guide apertures or cut-outs;
3-D printing a surgical corrected weight-bearing orthotic from the modified electronic image, said surgical orthotic including the one or more guide apertures or cut-outs.

According to a second aspect of the invention there is provided a surgical foot orthotic for the foot of a patient, the surgical foot orthotic being formed by the method according to the first aspect of the invention.

According to a third aspect of the invention there is provided a method of performing foot and/or ankle surgery on a patient in need thereof, the method comprising the steps of:
forming a surgical foot orthotic as defined in any one of paragraphs 1 to 7;
disposing the surgical foot orthotic about the foot of the patient and positioning same so as to manipulate bone articulation and joint congruency and establish the foot of the patient in the Windlass mechanism, or substantially as if the Windlass mechanism is engaged and the foot and bones of the foot are in the neutral or aligned position;
conducting a surgery on the foot and/or ankle of the patient whilst the surgical foot orthotic is disposed about the foot.

According to a fourth aspect of the invention there is provided, in a foot and/or ankle surgery of a patient, the use of a weight-bearing stance corrected foot orthotic adapted to be used on the foot of an anaesthetised patient in the supine or prone position, the weight bearing stance corrected foot orthotic adapted to dorsiflex the toes of the forefoot of the patient an angle of between 30° to 50° to the plane of the foot.

According to another aspect of the invention there is provided a method of performing foot and social ankle surgery on a patient in need thereof, the patient having a damaged foot requiring surgery and a foot not requiring surgery, method comprising the steps of:
forming a reference foot orthotic of the patient's foot not requiring surgery, the steps of forming the reference foot orthotic including:
disposing a patient's foot not requiring surgery in a weight bearing neutral position;
dorsiflexing the forefoot of the patient such that patient's foot is in or towards the Windlass mechanism thereof;
forming a first reference orthotic correcting the stance of the foot of the patient not requiring surgery in the weight bearing position with dorsiflexed forefoot;
scanning the first reference orthotic and forming an electronic image of the corrective load bearing surface thereof;
creating a mirror electronic image of the first reference orthotic such that the electronic mirror image is adapted to support the foot of the patient requiring surgery;

modifying the electronic mirror electronic image of the first reference orthotic to include one or more guide apertures or cut-outs;

3-D printing a surgical corrected weight-bearing orthotic from the modified mirror electronic image, said surgical orthotic including the one or more guide apertures or cut-outs;

disposing the 3-D printed surgical corrected weight-bearing orthotic about the foot of the patient in need of surgery;

positioning the 3-D printed surgical corrected weight-bearing orthotic to manipulate bone articulation and joint congruency and established the foot of the patient in need of surgery in the Windlass mechanism, or substantially as if the Windlass mechanism is engaged and the foot and bones of the foot requiring surgery are in the neutral or aligned position;

conducting a and invasive surgical procedure on the foot and/or ankle of the patient requiring surgery whilst the 3-D printed surgical corrected weight-bearing orthotic is disposed about the foot.

It can therefore be seen that there is advantageously provided a method of forming a surgical foot orthotic and production of an orthotic to correct the position and alignment of the foot of the patient in advance of a surgical procedure that helps the surgeon align the bones of the patient's foot as the surgery is being performed. When used with a method of performing surgery, this minimises the subjectivity and guesswork of the surgeon when aligning a foot during surgery. Furthermore, it will also allow for more predictable and repetitive surgical outcomes which benefits all parties. The use of the formed orthotics not only significantly assists the surgeon with position of the foot and hence the quality of the surgical procedure but also saves the surgeon time in achieving a desirable outcome. This also speeds up the time spent in surgery ultimately leading to an operative cost savings.

Yet further, in the preferred embodiments, a full length corrected surgical foot orthotic was used, with the forefoot portion angled at approximately 45 Degrees to the plane of the foot to assist in establishing the Windlass effect of the foot. Having the toes dorsiflexed, in conjunction with the corrected weight bearing neutral foot position provides a surprising improvement in conduct and outcome of foot and ankle surgeries to assist and maintain the best possible bone articulation and joint congruency of the foot.

BRIEF DESCRIPTION OF THE DRAWINGS

A preferred embodiment of the invention will now be described, by way of example only, with reference to the accompanying drawings in which:

FIGS. 3 to 6 show various images of the foot orthotic of FIGS. 1 & 2;

FIGS. 7 to 10 are computer screen shot images of a computer simulation of the foot orthotic of FIG. 6;

DETAILED DESCRIPTION

Figure 1:
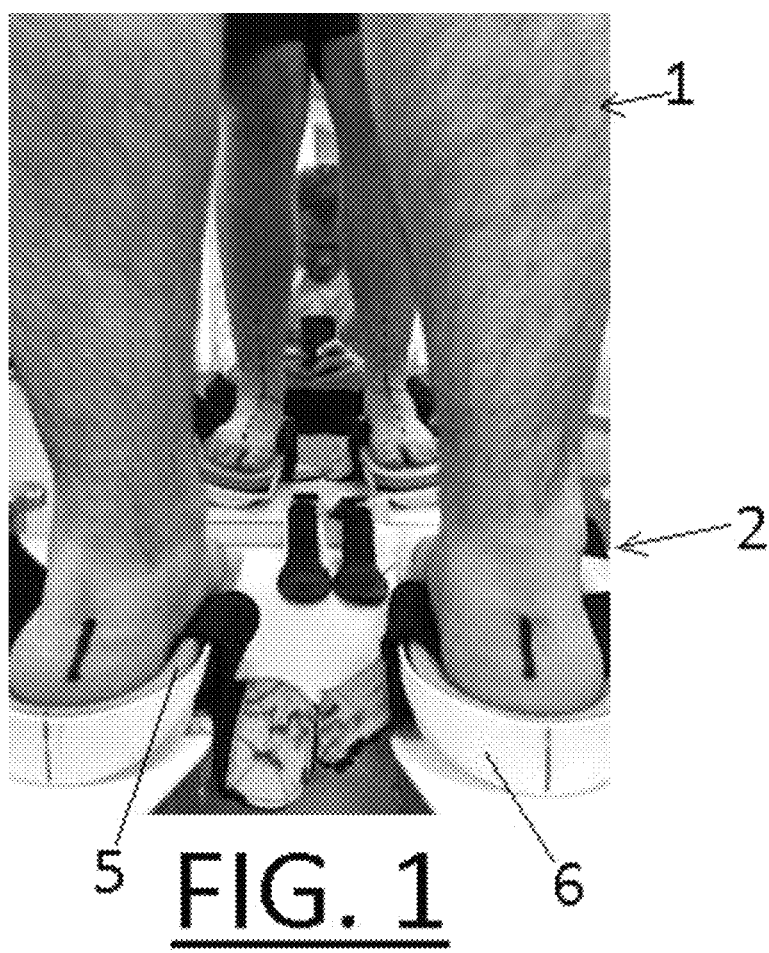
FIGS. 1 & 2 are photographs of the rear of a patient's lower legs in the process of correcting their stance under load for making a foot orthotic according to the preferred embodiment of the invention.

Referring to the drawings generally, like reference numerals are used to denote like components unless expressly noted otherwise. It will be understood the term "surgical foot orthotic" or the like is used to denote a foot orthotic configured for use in a surgical environment and includes an orthotic in sterile form per se or an orthotic enclosed in a suitably sterile bag or envelope. Further, it will be understood that the term "neutral position" or the like of the foot refers to an orthopaedic definition of subtalar neutral being the position in which the forefoot is locked on the rear-foot with maximum pronation of the midtarsal joint such that the foot is neither pronated or supinated. Yet further, it will be understood that whilst a surgical procedure of the ankle region of the foot connecting the lower leg thereto is described with reference to the preferred embodiment, it will be appreciated that the invention is applicable to surgeries of the foot, ankle region or lower leg immediately adjacent the ankle.

Figure 18:
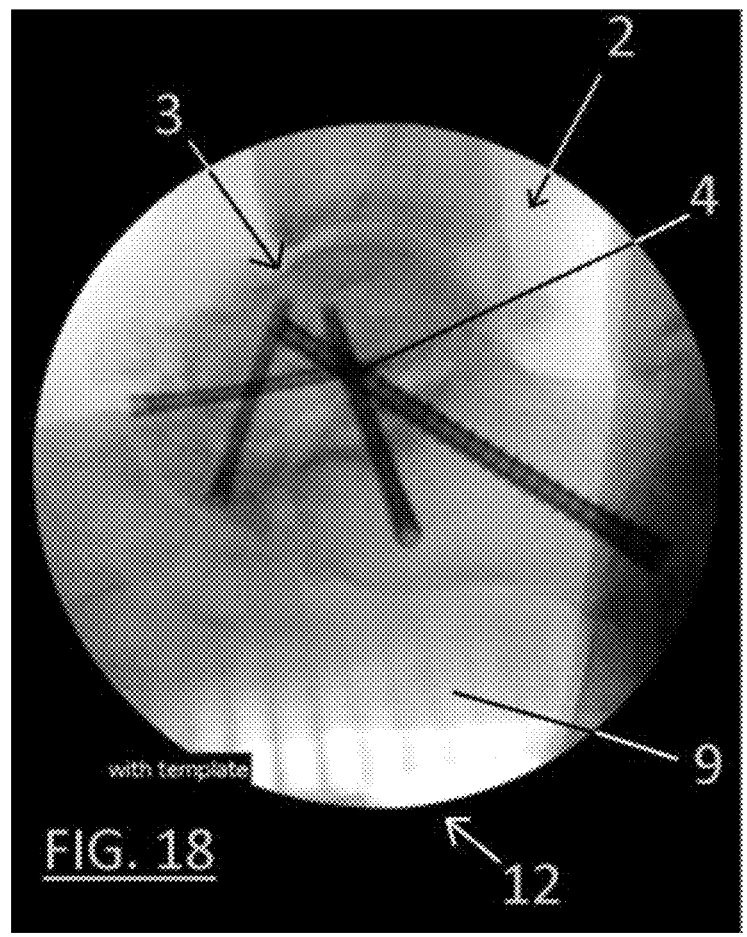
FIG. 18 is an X-ray of the ankle of part of the foot and ankle region of the patient after surgery.

The preferred embodiment of the invention is described with reference to a patient (1) having post-traumatic arthritis (3) of their foot (2) and in need of surgery to correct alignment and fuse arthritic joints. In the post-traumatic changes (3) of the patient (1), exhibited in the lateral X-Ray (side view) of FIG. 11, mechanical fasteners in the form of orthopaedic screws (4) are to be inserted in pre-determined locations in the foot. The surgically inserted screws (4) are shown in FIG. 18, being an X-ray of the foot/ankle region of the patient (1) after the surgery, as will be described later.

Figure 11:
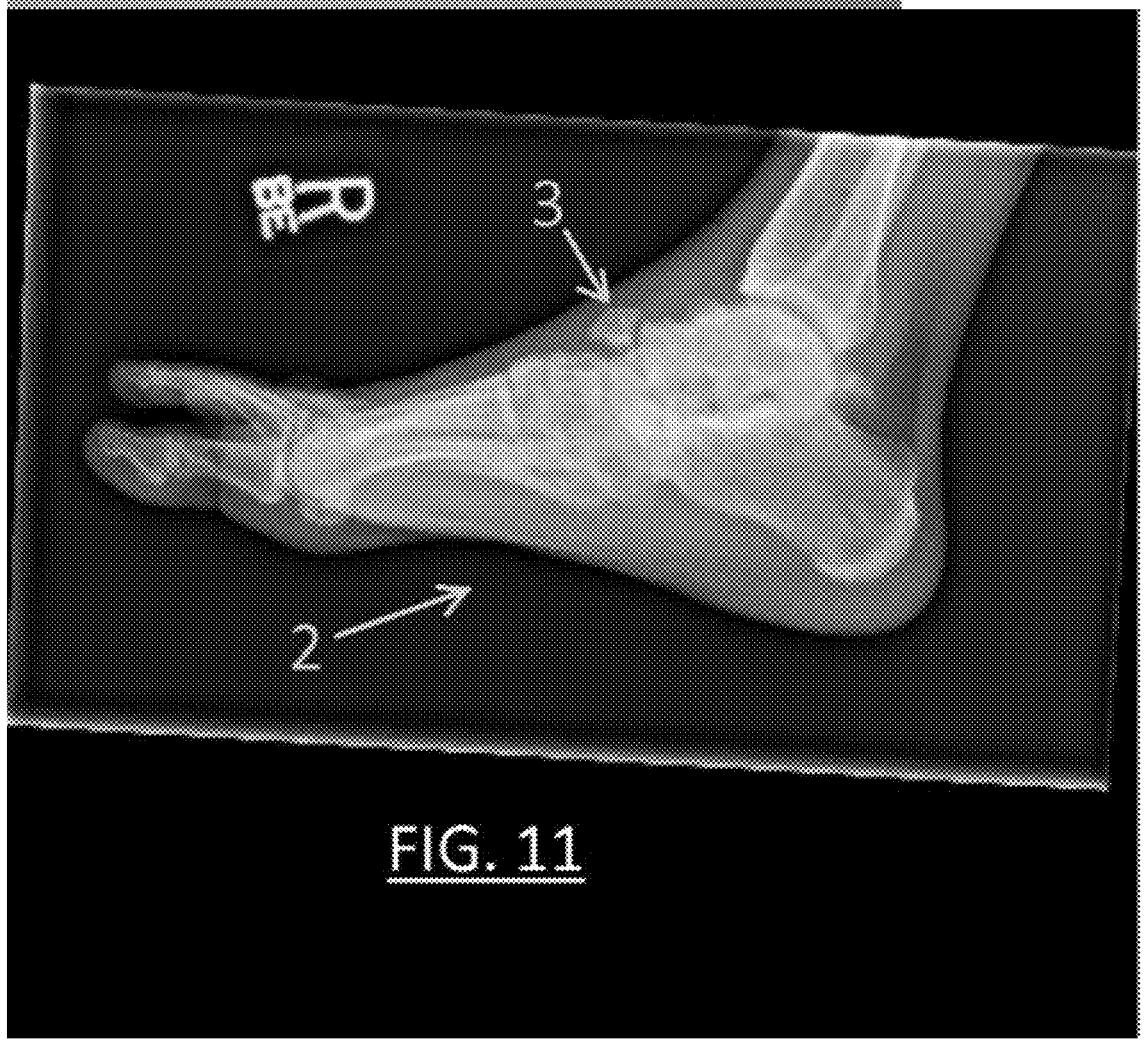
FIGS. 11 & 12 are X-ray images of the foot of the patient's damaged foot prior to surgery without and with a stance corrected orthotic according to the invention based on the orthotic of FIG. 6.

As can be seen from FIG. 11, the alignment and orientation of the foot/ankle has been altered secondary to the patient's previous trauma. In the preferred embodiment, a foot orthotic (5) for use during surgery to align the foot (2) of the patient (1) is provided. Prior to the surgery of the patient (1), a practitioner forms an orthotic for at least the foot (2) requiring surgery. Although not shown in the preferred embodiment it is generally preferable a pair of foot orthotics is formed.

Figure 2:
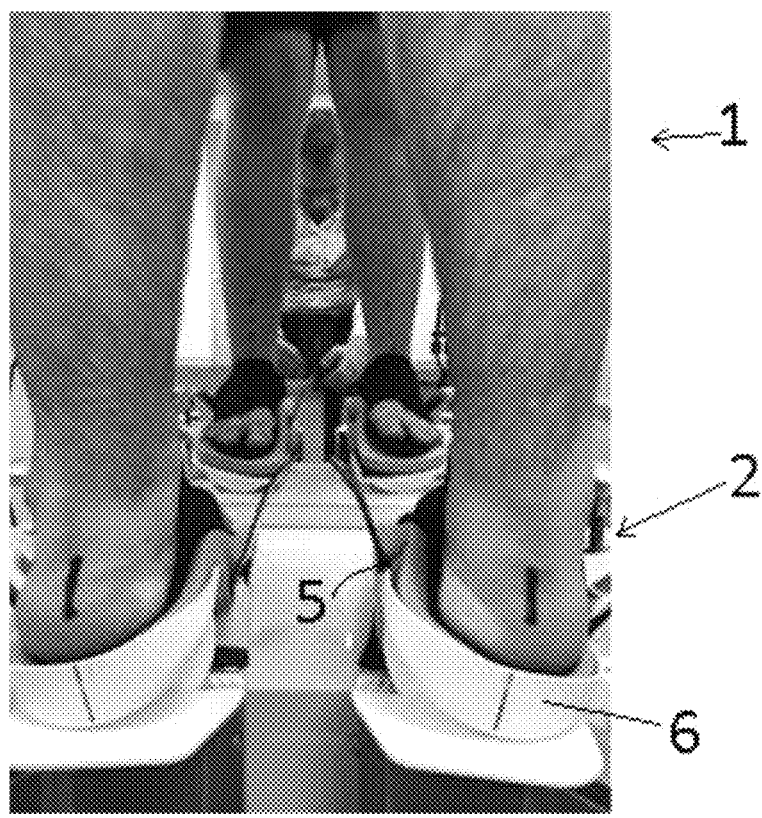
Figure 4:
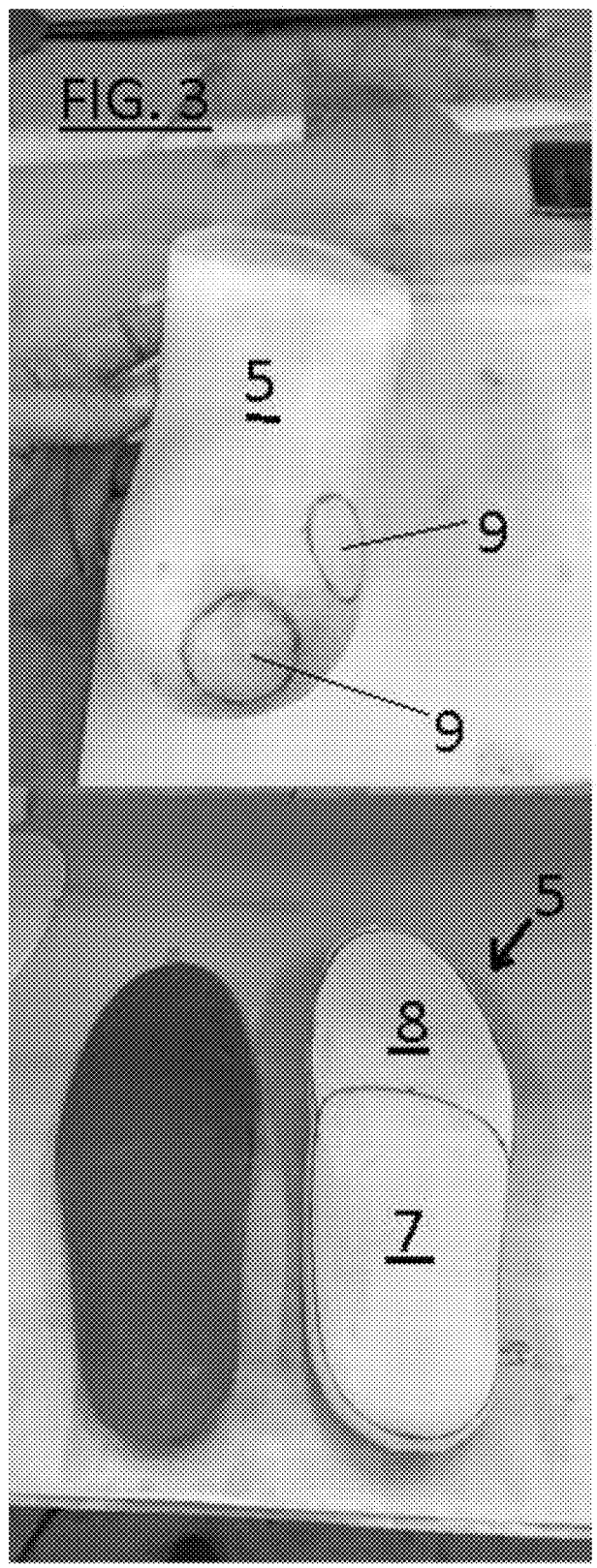
Figure 5:
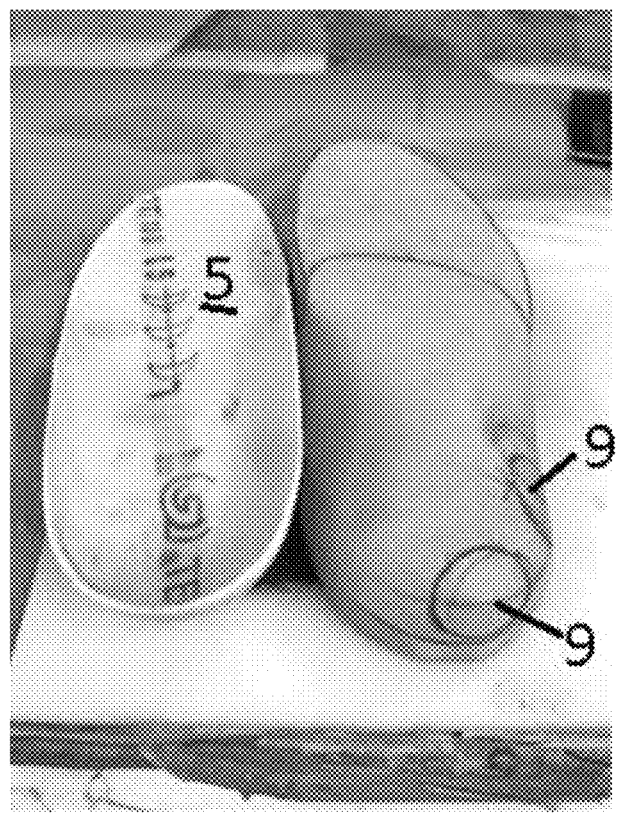
Figure 8:
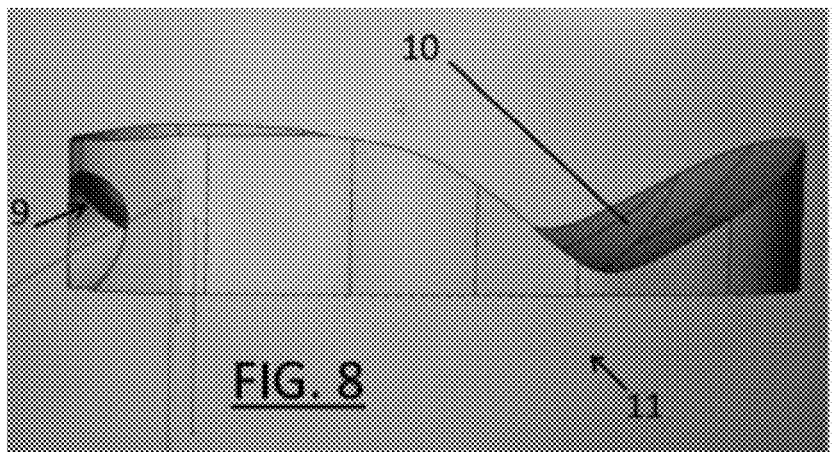
Figure 9:
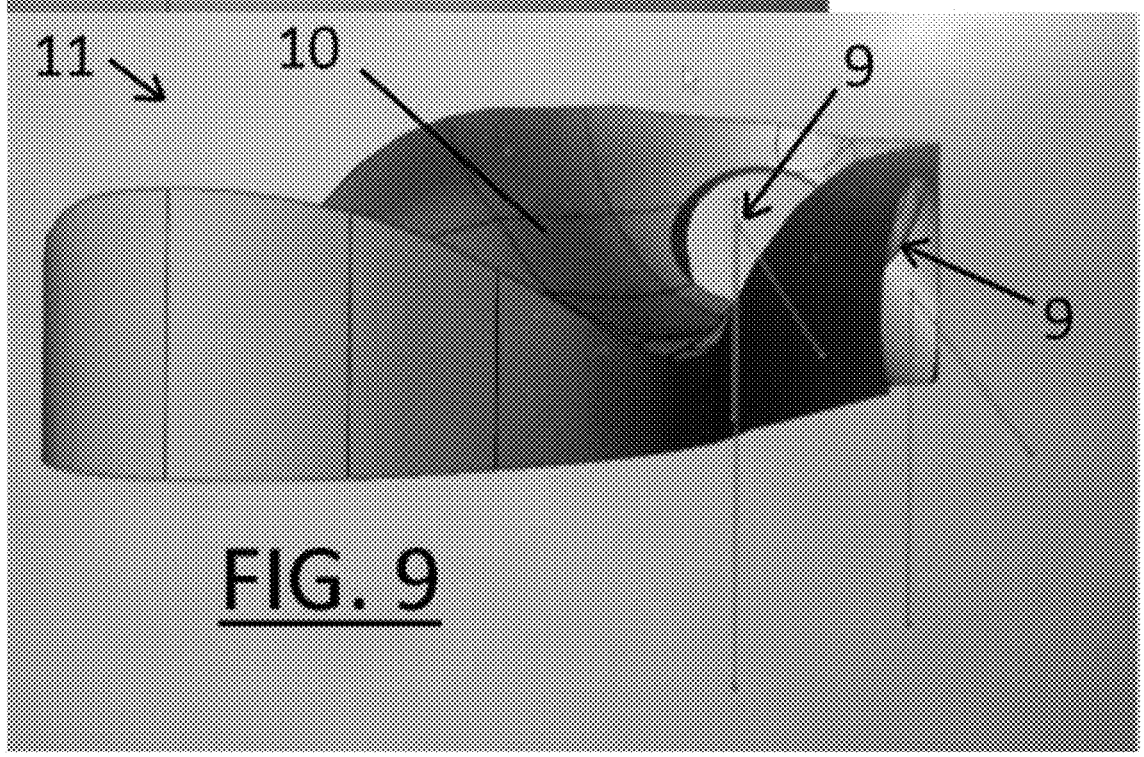
Figure 10:
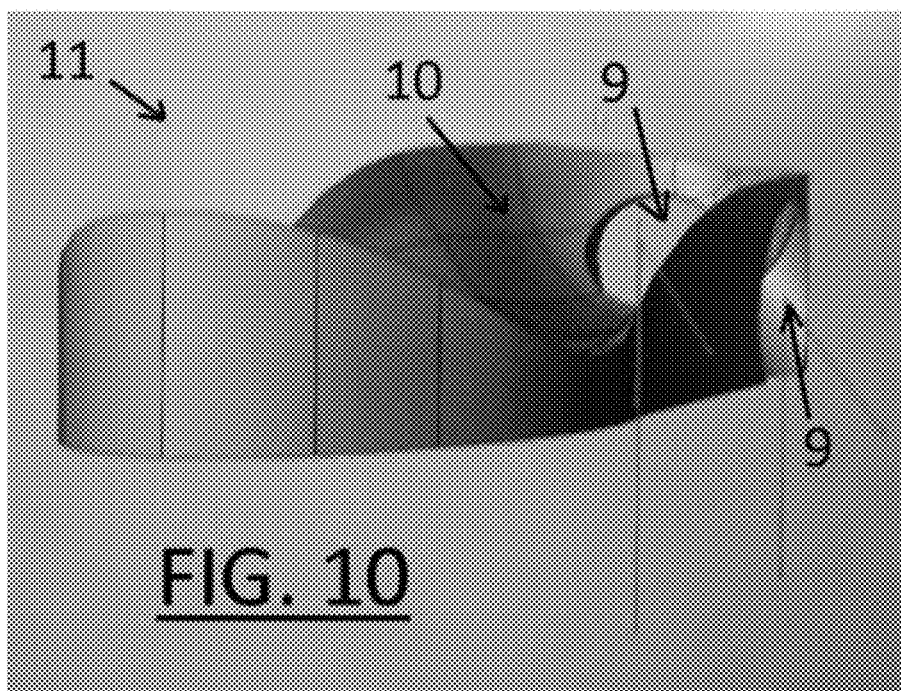

The formation of the foot orthotics is to align the feet of the patient to be in a weight—bearing neutral position. FIG. 1 is a photograph of the rear of the patient (1) (or the lower part of their legs) at the commencement of the process of preparing an orthotic. The misalignment of the left foot in the photo shows the magnitude of the departure from the weight-bearing neutral position of that foot (2). FIG. 2 is a photograph of the same patient with both feet moved into the corrected weight-bearing neutral position.

In the preferred embodiment, the formed orthotic (5) can be seen disposed intermediate each of the patient's feet (2) and a support surface (6). The feet of the patient are aligned in manner set forth and published in International Patent Application No. PCT/AU2014/050242 or U.S. Pat. No. 7,125,509. The latter patent forms an orthotic (5) using a plaster cast method and the former forms an orthotic (5) using mouldable thermoplastic materials. The disclosure of PCT/AU2014/050242 and U.S. Pat. No. 7,125,509 are both incorporated into the description of the preferred embodiment of the present invention in their entirety.

Before orthotic (5) is formed in the corrected position, the forefoot and toes on the foot (2) of the patient (1) are raised to engage the "Windlass mechanism" (also referred to as Windlass configuration). The dorsiflexing of the toes, particularly the great toe and preferably at an angle of between 30° to 50° and most preferably about 45°, causes the plantar fascia of the foot to tighten there by shortening the distance between the calcaneus and the metatarsals to elevate the medial longitudinal arch. This provides an optimal metier longitudinal arch position with the foot of the patient (1) in the neutral weight-bearing position. Once the toes are dorsiflexed and the Windlass mechanism engaged, the orthotic (5) is produced.

FIGS. 3 to 6 show aspect of orthotics (5) FIG. 3 shows a three quarter length support (7) that is attached to full length support (8) to form orthotic (5). It is noted in FIG. 3 that the three quarter length support (7) includes a pair of circles (9) (discussed later) drawn toward the heel end thereof. The final formed foot orthotic (5) is shown in FIG. 6.

The orthotic (5) of the foot (2) of the patient (1) in the weight-bearing neutral position with the Windlass mechanism formed is then scanned and an electronic image of the weight-bearing neutral position orthotic (5) is formed. In the preferred embodiment, this was preferably achieved by using a known laser scanner. The results of the scanned foot orthotic are shown in FIGS. 7 to 10 and the circles (9) shown in the three quarter length foot support orthotic (5) are shown translated into the electronic image.

The scanned electronic image of the orthotic (5) is adapted to form an electronic image of the load bearing surface of the foot orthotic (5). A substantially flat support sole is added so that the electronic image (10) only resembles the weight-bearing surface of the orthotic (5). The apertures (9) correspond to the circles shown in the three quarter mould support (7) (see FIG. 3). These apertures (9) of the orthotic (5) are electronically included so that they correspond to the correct location about the foot, where the apertures are required and also that their angle or pitch is substantially aligned with a preferred direction of insertion of the mechanical fastening screws (4) into the bone. FIGS. 7 to 10 show the electronic image of the orthotic (5) when for use in a surgery.

The electronic image of the orthotic show in FIGS. 7 to 10, is 3D printed in the preferred embodiment. The 3D printed orthotic is preferably printed from a nylon composite material able to be sterilised and autoclaved suitably for use in a surgical environment. In the preferred embodiment, however, the surgical orthotic (12) is enclosed in a sterile bag (13) providing a sealed/sterile environment for the orthotic (12) during use in surgery. However, it will be appreciated that the surgical orthotic (12) can be formed from any preferred 3-D printing substrate material that is able to be sterilised and autoclaved in accordance with local laws and regulations for use in operating theatre.

Figure 12:
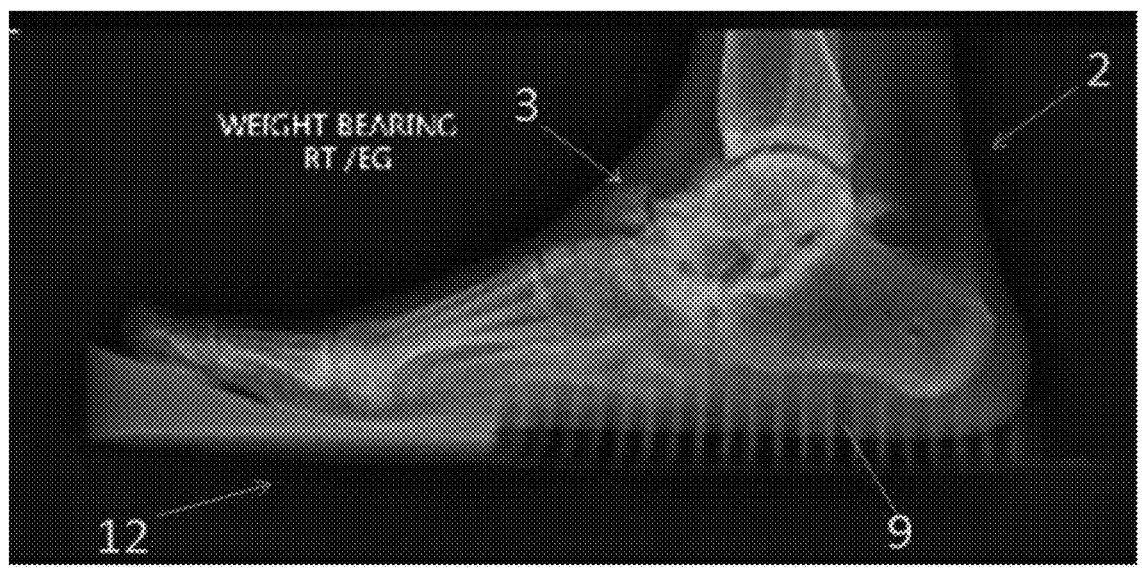
Figure 13:
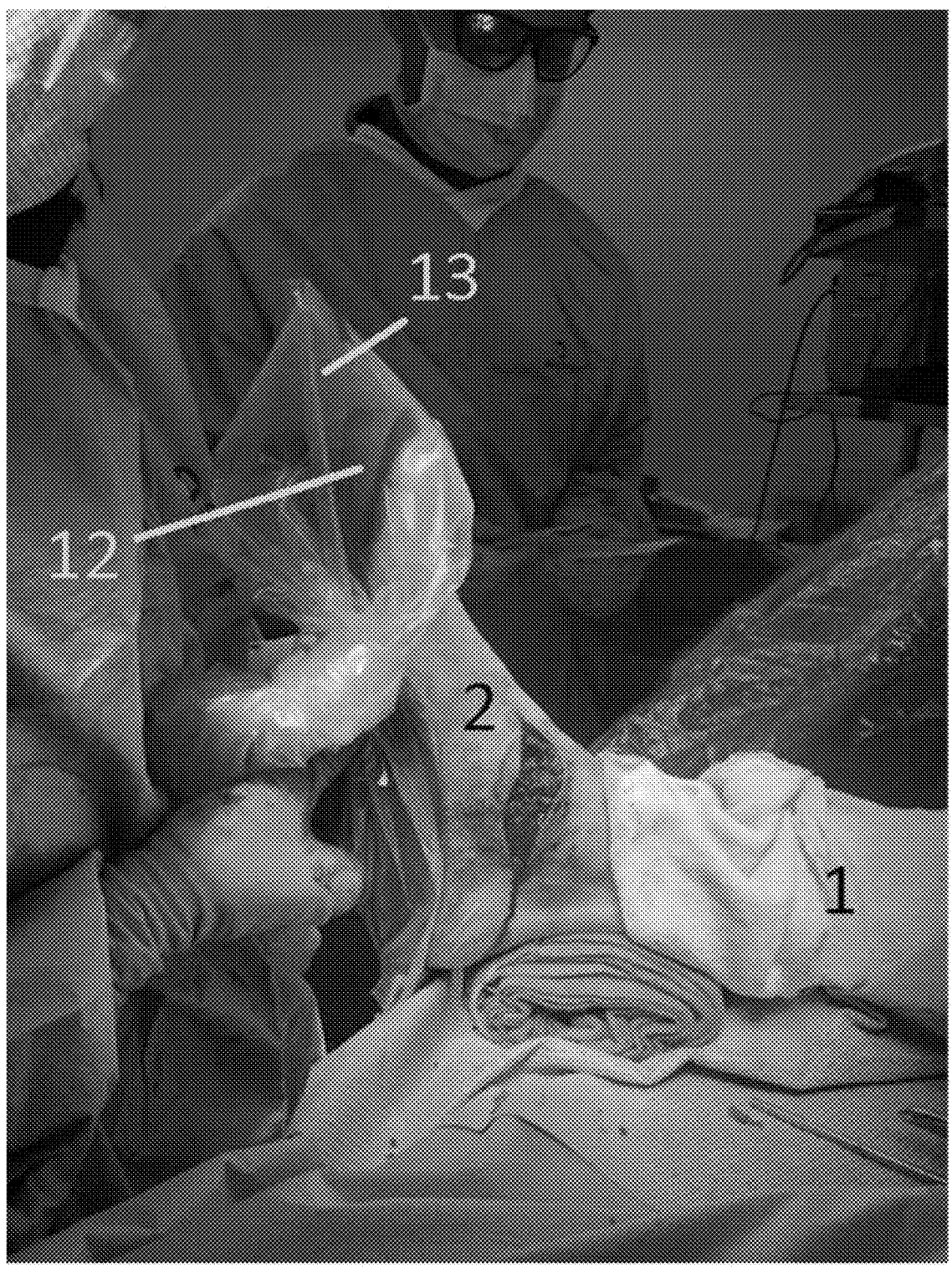
FIGS. 13 to 17 are photographs of the corrected foot orthotic of FIG. 12 being moved into contact with the patient's foot.
Figure 14:

FIG. 12 is an X-ray side view of the foot (2) of the patient (1) with the surgical orthotic (12) disposed under their feet. The foot (2) is aligned by the surgical orthotic (12) to assume the weight-bearing neutral position with the toes dorsiflexed to induce the Windlass mechanism. In this way, the foot (2) of the patient (1) can be advantageously continuously supported in a corrected position whilst the surgeon conducts their operation, in the preferred embodiment to insert fastening screws (4) to stabilise the rearfoot.

FIGS. 13 to 17 are various photographic images of the foot of the patient during surgery, two of the patient (1) in surgery where the surgical orthotic (12) sealed in a sterile bag (13) is a butted up against a bottom of the patient's foot (2) to move the foot into the weight-bearing neutral position immediately after joint preparation to allow the foot to be manipulated into a neutral position (or is close thereto as possible). Following the capturing of these images, screw fixation was placed to maintain the corrected position of the patient's foot.

Figure 15:
Figure 16:
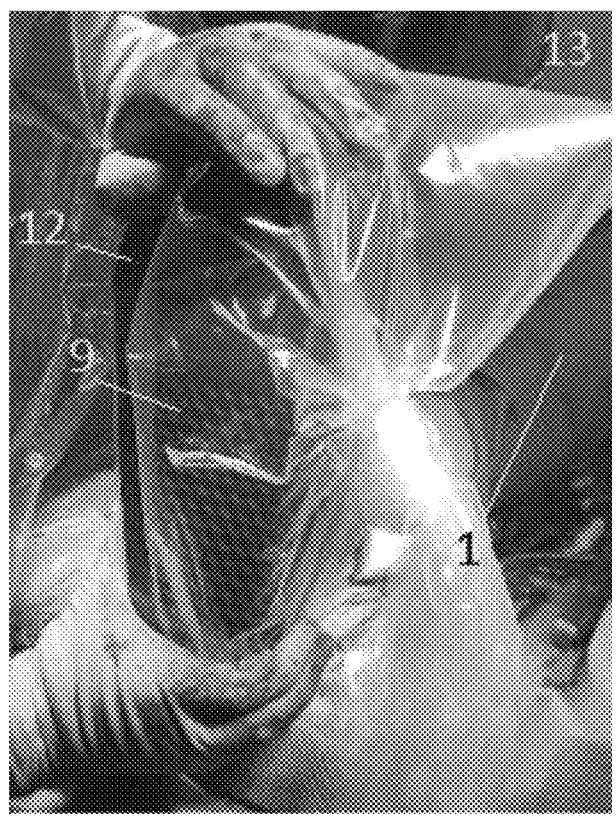
Figure 17:
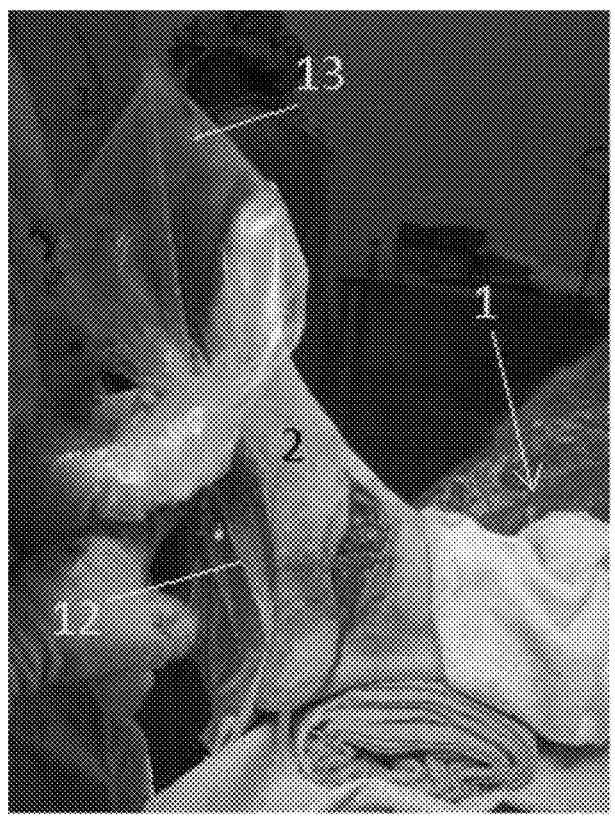

As best seen in FIG. 15, the toes of the foot (2) are dorsiflexed when the orthotic is moved in place under the foot (2) at this time. The surgeon uses apertures (9) of the surgical orthotic (12) for access to the foot where fastening screws (4) are inserted into the ankle region to stabilise it to allow it to properly heal. FIG. 18 shows screws (4) inserted into the foot (2) with the patient still in a supine position with a surgical orthotic (12) clearly visible below.

Whilst it is most ideal to dorsiflex the toes of the patient by approximately 45 degrees to the plane of the foot (2), it will be appreciated that this angle need not be 45 degrees and maybe some angle approaching this is a best approximation to engage in the Windlass mechanism. It is also noted with reference to FIG. 12, below the foot (2) of the patient the surgical orthotic (12) is shown (a forefoot portion) to be substantially solid and the mid and rear foot portion include apertures through the sole to allow for temporary and/or permanent fixation of the foot. It is noted that the apertures (9) shown in the mid and rearfoot portion are positioned as holes for a guide so that the surgeon can drill into the bones of the foot (2) and then screw a fixation in place while the foot is being held in the neutral position.

Although not clearly shown, it will be appreciated that the surgical orthotic (12) can be disposed under the foot (2) of the patient (1) and its position can be checked visually by the surgeon to ensure the foot is properly aligned and the Windlass mechanism engaged, or an X-ray may be taken such as shown in FIG. 12. It will be appreciated that the foot orthotic (12) can include alignment indicia adapted to correspond to a feature or indicia disposed on a foot (2) of the person, to ensure that the orthotic (12) is properly fitted to the foot (2) to move it into the weight-bearing neutral position with the toes dorsiflexed.

In another preferred embodiment of the invention, the above mentioned method and preparation and use of the surgical orthotic (5) can be altered to assist in the corrective surgery the foot and/or ankle that is too badly damaged or deformed to be able to place the foot of the patient in a weight-bearing neutral position so as to form the first orthotic. It will be appreciated that there can be many clinical reasons why the foot of a patient requiring surgery cannot be moved into a weight-bearing neutral position with the forefoot dorsiflexed.

For example, a common condition known as Charcot foot which is a condition caused generally by significant peripheral neuropathy or nerve damage in the feet where bones are weakened to an extent that they are easy to fracture and the sufferer continues to walk on the foot and use it normally as they cannot feel pain or other sensations because of the nerve damage. The shape of a foot can eventually change shape and the ankle joint is known to collapse where the foot has an abnormal shape known as "rocker-bottom". This condition is particularly serious including in patients suffering diabetes and failure to properly treat Charcot foot can result in severe deformity of the foot, disability of the person and even amputation.

In such cases with a foot requiring surgery cannot bear load for the production of the surgical orthotic, the above method is modified so that the first orthotic is formed from the patient's foot which is not damaged or in need of surgery and is able to be placed in a weight-bearing neutral position. The first orthotic in this preferred embodiment can be termed a first reference foot orthotic of the patient's foot not requiring surgery.

More particularly, the reference foot orthotic is formed by disposing a patient's foot not requiring surgery in a weight bearing neutral position and their forefoot is dorsiflexed such that patient's foot is in or towards the Windlass mechanism thereof. The first reference orthotic correcting the stance of the foot of the patient not requiring surgery in the weight bearing position with dorsiflexed forefoot. This reference orthotic is scanned and an electronic image of the scanned corrective load bearing surface is created.

So far as the electronic image of the reference orthotic is to the foot of the patient not requiring surgery, a mirror image of the electronic image of the first reference orthotic is produced. The electronic mirror image is adapted to support the foot of the patient requiring surgery whereby the foot not requiring surgery provides a reference template when the foot requiring surgery is unable to bear load, or the like.

The first reference orthotic mirror image is modified as per the above described method to include one or more guide apertures or cut-outs. From the first reference orthotic mirror image, a 3-D printed surgical corrected weight-bearing orthotic is then produced. The orthotic is produced by this method advantageously provide a practical reference point from which a surgical orthotic for a foot in need of surgery can be formed.

In the surgical theatre, the 3-D printed surgical corrected weight-bearing orthotic is positioned about the foot of the patient in need of the surgery most preferably once they are anaesthetised. This assists in the manipulation of the foot of the patient requiring surgery to match the weight-bearing surface of the 3-D printed surgical orthotic whereby its positioning manipulates bone articulation and joint congruency and establishes the foot of the patient in need of surgery in the Windlass mechanism, or substantially as if the Windlass mechanism is engaged and the foot and bones of the foot requiring surgery are in the neutral or aligned position. An invasive surgical procedure on the foot and/or ankle of the patient requiring surgery whilst the 3-D printed surgical corrected weight-bearing orthotic is disposed about the foot is then conducted.

Above, it is noted that the 3-D printed surgical corrected weight-bearing orthotic is formed from the scanned electronic image of the orthotic (5). However, it will be appreciated by those skilled in the art that the electronic image of the orthotic (5) can be transferred to a block of material that is milled to form the load bearing surface of the orthotic (5) such as with a CNC milling machine or similar. In this case, a template can have a load bearing surface cut to form the shape of the orthotic (5) so that the foot will be in foot corrected position. Of course, 3-D printing is preferred as currently such printers are significantly less expensive to purchase and less complicated to operate than a CNC milling machine, for example.

In another preferred embodiment of the invention, the aforementioned methods can be additionally modified to assist in performing a surgery where a patient cannot in practice be used to form a weight-bearing neutral position orthotic. For example, in an emergency or trauma situation where the patient may be unresponsive even where damage to their foot and/or ankle may not normally be so significant as to not be able to bear load and form orthotic (5). In these circumstances, it is preferred that rather than forming surgical orthotic (12) with one or other foot of the patient, pre-fabricated surgical orthotics (12) can be employed. In other circumstances, a surgeon may require additional stability of the foot for the performance of a surgery.

Pre-fabricated surgical orthotics (12) are preferably provided over a range of sizes to correspond to the size of the foot of a patient that may be required. Further, the sizes are preferably provided in respect of surgical orthotics (12) that are adapted particularly for a male foot, a female foot or a child's foot. The prefabricated surgical orthotics (12) are, of course, able to be fully sterilised or placed in a sterile bag for use in a surgical environment and formed by 3-D printing, moulding or computer controlled milling techniques. The prefabricated orthotics (12) for each foot size can come in a range of common corrections including for high and low arches, average arches and where the toes of the surgical orthotic (12) may or may not be angled to engage the Windlass mechanism (i.e. dorsiflexion of toes) depending on whether the foot of the metatarsals on the foot of a patient are too rigid to engage the Windlass mechanism. In this way, the surgeon can select the prefabricated surgical orthotic (12) at the time of the surgery, such as in emergency or trauma situations or simply when stabilisation of the foot is required, depending on the foot size of the patient and what apparent support may be required such as for arch height and any engagement of the Windlass mechanism.

Furthermore, it will be appreciated that one or more apertures (9) can also be included in prefabricated surgical orthotics (12) to provide access to the foot by a surgeon through the surgical orthotic (12). This can be to allow the performance of any number of surgical techniques such as the insertion of fasting screws into the bones of a foot to fix it into position.

Whilst it is appreciated that use of prefabricated surgical orthotics (12) may not be as desirable for an accurate surgical outcome as either using the actual foot of the patient requiring surgery to provide a weight-bearing neutral position orthotic (5) or even mirroring a weight-bearing neutral position orthotic (5) is formed from a good foot for use in another, the use of prefabricated surgical orthotics (12) offers a distinct advantage in many circumstances where it is impractical for the patient to bear weight on their foot requiring surgery.

Lastly, it will be appreciated where there are circumstances in which an assistant is not available to the surgeon to maintain the location of the surgical orthotic (12) on the foot of a patient during the actual surgery. That is, a surgeon orients the surgical orthotic (12) into a position relative to the foot they are satisfied with and the orthotic (12) is then maintained in place by an assistant while the surgeon operates on the foot. When the assistant is not available, it is preferable to have a jig or the like to support the orthotic in place on the bottom of the foot while the surgeon operates.

Such a jig must be sterilisable or be able to be placed in a sterile bag for example for use in a surgical environment and can be formed from any preferred material. In most preferred embodiment, a L-shaped support can be used whereby the vertical portion of the L is positioned underneath the lower portion of the leg of a patient and the horizontal portion of the L is positioned adjacent the bottom of the foot on which surgery is being prepared with orthotic (12) is disposed intermediate. The orthotic (12) is held in place by the patient's weight on the vertical portion of the L.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. A method of performing foot and/or ankle surgery on a patient in need thereof, the method comprising the steps of:
   forming a surgical foot orthotic; by the steps of:
   disposing a patient's foot or both feet in a weight bearing neutral position;
   dorsiflexing all or part of the forefoot or forefeet of the patient such that patient's foot or feet are in or towards the Windlass configuration thereof;
   forming a first orthotic correcting the stance of the patient in the weight bearing neutral position with dorsiflexed forefoot;
   scanning the first orthotic and forming an electronic image of the corrective load bearing surface thereof;
   modifying the electronic image to include one or more guide apertures or cut-outs, each aperture or cut-out configured to receive a surgical apparatus therethrough; and
   3-D printing the surgical foot orthotic from the modified electronic image, said surgical foot orthotic being a surgical corrected weight-bearing orthotic including the one or more guide apertures or cut-outs;
   disposing the surgical foot orthotic about the foot of the patient and positioning same so as to manipulate bone articulation and joint congruency and establish the foot of the patient in or towards the Windlass mechanism, and the foot and bones of the foot are in the neutral or aligned position; and
   conducting an invasive surgery on the foot and/or ankle of the patient whilst the surgical foot orthotic is disposed about the foot.

2. The method according to claim 1 wherein the forefoot is dorsiflexed by an angle of between 30° to 50°, or at approximately 45°, to the plane defined by the foot.

3. The method according to claim 1 wherein the first orthotic is formed from a heat mouldable template.

4. The method according to claim 1 wherein the surgical foot orthotic is 3-D printed from a nylon or nylon composite material or other autoclavable and sterilisable material.

5. The method according to claim 1 wherein the step of dorsiflexing the forefoot includes dorsiflexing all toes on the foot of a patient.

6. The method according to claim 1 including the step of providing indicium on the surgical foot orthotic, the indicium corresponding to a predetermined alignment point on the foot of the patient.

7. The method according to claim 1 including the step of sterilising or autoclaving the surgical foot orthotic.

8. A method of performing foot and/or ankle surgery on a patient in need thereof, the patient having a damaged foot requiring surgery and a foot not requiring surgery, method comprising the steps of:
   forming a reference foot orthotic of the patient's foot not requiring surgery, the steps of forming the reference foot orthotic including:
   disposing a patient's foot not requiring surgery in a weight bearing neutral position;
   dorsiflexing the forefoot of the patient such that patient's foot is in or towards the Windlass mechanism thereof;
   forming a first reference orthotic correcting the stance of the foot of the patient not requiring surgery in the weight bearing position with dorsiflexed forefoot;
   scanning the first reference orthotic and forming an electronic image of the corrective load bearing surface thereof;
   creating a mirror electronic image of the first reference orthotic such that the electronic mirror image is adapted to support the foot of the patient requiring surgery;
   modifying the mirror electronic image of the first reference orthotic to include one or more guide apertures or cut-outs; and
   3-D printing a surgical corrected weight-bearing orthotic from the modified mirror electronic image, said surgical orthotic including the one or more guide apertures or cut-outs;
   disposing the 3-D printed surgical corrected weight-bearing orthotic about the foot of the patient in need of surgery;
   positioning the 3-D printed surgical corrected weight-bearing orthotic to manipulate bone articulation and joint congruency and established the foot of the patient in need of surgery in the Windlass mechanism, or substantially as if the Windlass mechanism is engaged and the foot and bones of the foot requiring surgery are in the neutral or aligned position; and
   conducting an invasive surgical procedure on the foot and/or ankle of the patient requiring surgery whilst the 3-D printed surgical corrected weight-bearing orthotic is disposed about the foot.

* * * * *